United States Patent
Tirén (10) Patent No.: US 10,431,413 B2
(45) Date of Patent: Oct. 1, 2019

(54) X-RAY SOURCE AND SYSTEM COMPRISING AN X-RAY SOURCE

(71) Applicant: Lightlab Sweden AB, Uppsala (SE)

(72) Inventor: Jonas Tirén, Uppsala (SE)

(73) Assignee: LIGHTLAB SWEDEN AB, Uppsala (SE)

( * ) Notice: Subject to any disclaimer, the term of this patent is extended or adjusted under 35 U.S.C. 154(b) by 306 days.

(21) Appl. No.: 15/503,455

(22) PCT Filed: Aug. 31, 2015

(86) PCT No.: PCT/EP2015/069820
§ 371 (c)(1),
(2) Date: Feb. 13, 2017

(87) PCT Pub. No.: WO2016/034526
PCT Pub. Date: Mar. 10, 2016

(65) Prior Publication Data
US 2017/0236677 A1    Aug. 17, 2017

(30) Foreign Application Priority Data

Sep. 1, 2014 (EP) .................................... 14183041

(51) Int. Cl.
*H01J 35/06*    (2006.01)
*H01J 35/08*    (2006.01)
(Continued)

(52) U.S. Cl.
CPC .............. *H01J 35/065* (2013.01); *A61L 9/16* (2013.01); *B03C 3/08* (2013.01); *B03C 3/09* (2013.01); *B03C 3/12* (2013.01); *B03C 3/155* (2013.01); *B03C 3/383* (2013.01); *B03C 3/47* (2013.01); *C02F 1/307* (2013.01); *H01J 35/08* (2013.01); *H01J 35/16* (2013.01); *H05G 1/32* (2013.01); *A61L 2209/11* (2013.01);
(Continued)

(58) Field of Classification Search
CPC combination set(s) only.
See application file for complete search history.

(56) References Cited

U.S. PATENT DOCUMENTS 3,340,680 A * 9/1967 Fields ....................... A61L 9/01
                                                        422/4
3,735,187 A * 5/1973 Rogers .................. H01J 35/065
                                                        313/336

(Continued)

FOREIGN PATENT DOCUMENTS

DE        10144448        3/2003
JP        H0838844        2/1996
(Continued)

OTHER PUBLICATIONS

Chiara Giovanardi; International Search Report, parent application PCT/EP2015/069830, dated Nov. 5, 2015, European Patent Office, Rijswijk NL.

Primary Examiner — Amber R Orlando
Assistant Examiner — Sonji Turner
(74) Attorney, Agent, or Firm — Babcock IP, PLLC (57) ABSTRACT

The present invention generally relates to an x-ray source and specifically to an x-ray source suitable for large area x-ray generation. The invention also relates to a system comprising such an x-ray source.

11 Claims, 6 Drawing Sheets

(51) Int. Cl.
*H05G 1/32* (2006.01)
*A61L 9/16* (2006.01)
*B03C 3/47* (2006.01)
*B03C 3/155* (2006.01)
*B03C 3/09* (2006.01)
*C02F 1/30* (2006.01)
*H01J 35/16* (2006.01)
*B03C 3/08* (2006.01)
*B03C 3/12* (2006.01)
*B03C 3/38* (2006.01)
*B01D 53/32* (2006.01)
*C02F 1/00* (2006.01)
*C02F 103/00* (2006.01)

(52) U.S. Cl.
CPC .......... *B01D 53/32* (2013.01); *B01D 2257/91* (2013.01); *B01D 2258/06* (2013.01); *B01D 2259/81* (2013.01); *C02F 1/001* (2013.01); *C02F 2103/008* (2013.01); *C02F 2209/003* (2013.01); *C02F 2209/005* (2013.01); *C02F 2209/36* (2013.01); *C02F 2303/04* (2013.01); *H01J 2235/068* (2013.01)

(56) References Cited

U.S. PATENT DOCUMENTS

| | | | | |
|---|---|---|---|---|
| 5,014,289 A * | 5/1991 | Rothe | ............ | H01J 35/04 378/119 |
| 5,159,697 A * | 10/1992 | Wirth | ............ | H01J 35/16 378/101 |
| 5,729,583 A * | 3/1998 | Tang | ............ | A61B 6/145 378/122 |
| 6,008,575 A * | 12/1999 | Kaftanov | ............ | H01J 1/304 313/309 |
| 6,477,233 B1 * | 11/2002 | Ribbing | ............ | A61N 5/1001 378/119 |
| 6,775,353 B2 * | 8/2004 | Thandiackal | ............ | H01J 35/16 378/119 |
| 6,873,095 B1 * | 3/2005 | Kjellman | ............ | B82Y 10/00 313/309 |
| 9,006,964 B2 * | 4/2015 | Hu | ............ | H01J 1/304 313/309 |
| 2003/0081730 A1 * | 5/2003 | Thandiackal | ............ | H01J 35/16 378/121 |
| 2005/0276382 A1 | 12/2005 | Lesiak | | |
| 2007/0237296 A1 | 10/2007 | Wyatt | | |
| 2008/0187093 A1 * | 8/2008 | Price | ............ | H01J 1/32 378/19 |
| 2008/0267354 A1 * | 10/2008 | Holm | ............ | H01J 33/00 378/122 |
| 2011/0087062 A1 * | 4/2011 | Hornig | ............ | H01J 35/065 600/3 |
| 2011/0286581 A1 * | 11/2011 | Sprenger | ............ | H01J 35/04 378/113 |
| 2011/0305312 A1 * | 12/2011 | Hu | ............ | H01J 35/065 378/4 |
| 2012/0027177 A1 * | 2/2012 | Ogata | ............ | H01J 35/065 378/95 |
| 2013/0175222 A1 * | 7/2013 | Spittle | ............ | C02F 1/004 210/683 |
| 2014/0185774 A1 * | 7/2014 | Wang | ............ | H05G 1/10 378/104 |
| 2014/0224996 A1 * | 8/2014 | Case | ............ | H01J 35/14 250/396 ML |
| 2015/0124932 A1 * | 5/2015 | Wang | ............ | H05G 1/56 378/111 |
| 2015/0348737 A1 * | 12/2015 | Nakamura | ............ | H01J 35/06 378/101 |
| 2015/0382440 A1 * | 12/2015 | Nakamura | ............ | H01J 35/06 378/101 |

FOREIGN PATENT DOCUMENTS

| | | | |
|---|---|---|---|
| JP | H0919646 | * | 1/1997 |
| JP | 2006043550 | | 2/2006 |
| WO | 2012023665 | | 2/2012 |

* cited by examiner

X-RAY SOURCE AND SYSTEM COMPRISING AN X-RAY SOURCE

TECHNICAL FIELD

The present invention generally relates to an x-ray source and specifically to an x-ray source suitable for large area x-ray generation. The invention also relates to a system comprising such an x-ray source.

BACKGROUND OF THE INVENTION

Systems for generation of x-ray radiation are used, for example, in medical diagnostics in order to acquire radiographic images or to produce planar images for technical diagnostic applications. One further effective use of x-ray radiation is in the treatment of substances to reduce the impact of biological and other contamination. For example, food can be irradiated to prolong useful life, making the food safer to consume. Waste water or runoff may be irradiated in the same manner to reduce the effects of contamination.

In the field of technical diagnostic imaging, x-rays are especially effective at penetrating internal structures of a solid object to be examined, and the images formed by the x-rays that pass there through reveal internal flaws or structural defects of the object. Technical diagnostic x-ray imaging thus provides a valuable quality control inspection tool for evaluating structural aspects of a product during manufacture and over the useful life of the product. This form of diagnostic analysis is sometimes advantageous over other types of evaluation, since the imaging object need not be destroyed in the process of the evaluation. For this reason, technical diagnostic imaging is also known as non-destructive testing.

Figure 1A:
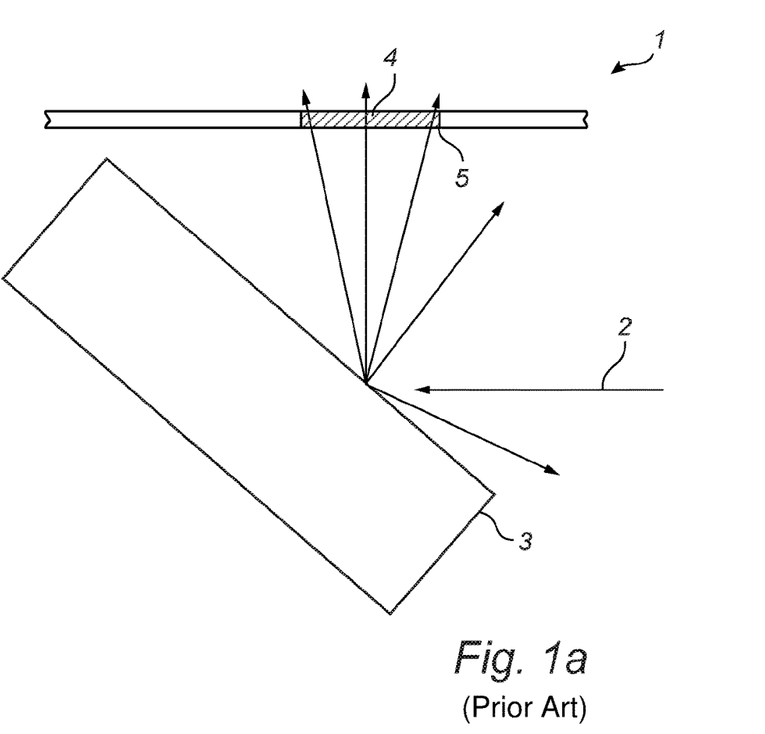
FIGS. 1a and 1b illustrate a prior art spot x-ray arrangement and the x-ray distribution from such an x-ray arrangement, respectively.
Figure 1B:
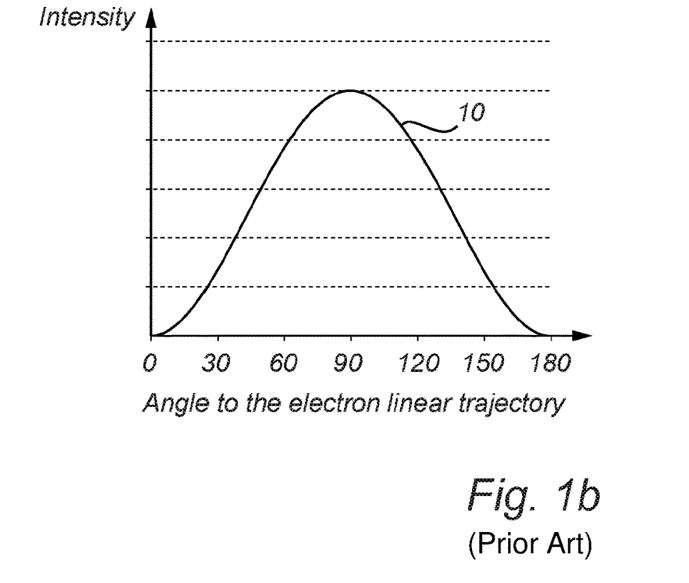

A typical prior-art arrangement is schematically illustrated in FIG. 1a. An x-ray tube, 1, typically comprises an electron gun having a cathode (not shown) that emits a beam of electrons, 2, that are accelerated to an anode 3. The anode is comprised of a metal target surface, such as tungsten, from which x-rays, 4, are generated due to the impact of the accelerated electrons. The radiation is composed of two parts, bremsstrahlung and characteristic radiation. Bremsstrahlung is the major part and is radiated with an intensity profile that has its maximum perpendicular to the linear path of the electron beam, 2, and has a distribution proportional to the angel by $\sin^2 (v)$ (where v=0 is the angle parallel to the electron linear motion i.e. the bremsstrahlung radiation intensity maximum is perpendicular to the electron beam path, 2), while the characteristic radiation has a uniform intensity distribution over a full solid angle (spherical). A sin 2 distribution 10 is shown in FIG. 1b, where the radial bremsstrahlung intensity from the electron path is shown to be uniform. Accordingly, and as can bee seen from FIG. 1a, the anode 3 is commonly placed at an angle to the axis of the electron beam, 2, the x-rays, 4, may be transmitted in a direction generally perpendicular to the electron beam axis. It should be noted that roughly half of the generated x-rays will penetrate into the anode in this arrangement and this will be absorbed. The x-rays, 4, may then be passed through a thin beryllium window 5 used to collimate the x-ray beam and also provide a vacuum seal within the x-ray tube 1. Thereafter, the x-rays 4 exit the x-ray tube 1 along a generally conical path where the apex of the cone is roughly coincident with the spot on target formed by the impinging electron beam.

This divergent radiation pattern, originating essentially from a point source will have an intensity fall off in vacuum, proportional to the inverse square of the distance r, i.e. $1/r^2$ for pure geometrical reasons. To effectively employ this radiation pattern at proper doses, radiation doses accounting for the fall off with distance, must be generated, and the object of interest must be positioned properly in the radiation cone. Although some radiation sources use multiple point sources, or one or more mobile point sources, to make up for the suboptimal emission pattern, such systems have their own inherent drawbacks and complexities. In particular, complications involving source timing, positioning, etc. are commonplace In the treating of materials for decontamination or sanitation purposes in particular, it is important to be able to deliver a sufficiently uniform and sufficiently strong radiation pattern so as to ensure adequate radiation to reduce the impact of microorganisms (or larger organisms) and contaminants.

Figure 2:
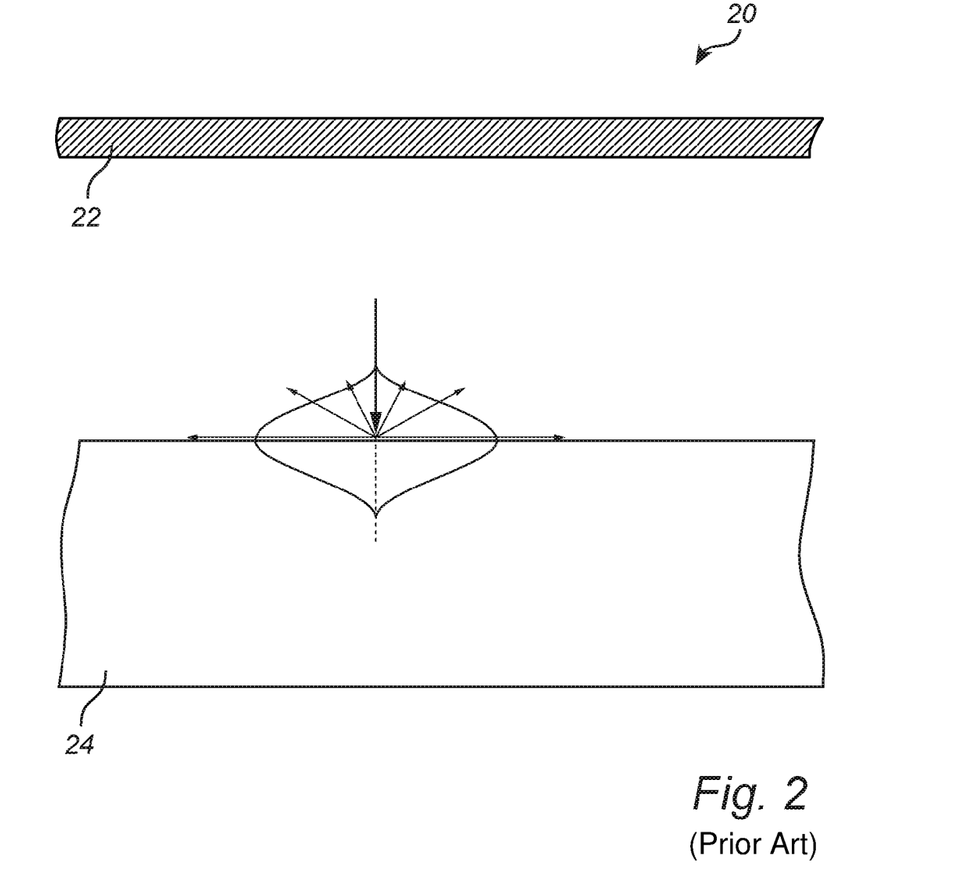
FIG. 2 illustrates the x-ray distribution pattern generated in a prior art flat panel x-ray arrangement.

One approach has been made to solve the above mentioned problems by the introduction of a large area flat panel source for x-ray generation. An example of such an implementation is disclosed in EP1948249, in which the one or more large area flat panel sources of x-ray radiation are directed into a target zone. A target substance to be treated is placed within the target zone, such as via conveyor belt, pipe, etc., and is irradiated with radiation from the one or more flat panel sources to reduce the biological effects of the contaminant presence in the target substance. A drawback with this solution is the distribution of the intensity where a large portion is lost as it is transmitted parallel or close to parallel to the surface. FIG. 2 conceptually illustrates the x-ray distribution in a prior art flat panel x-ray arrangement 20, comprising a transmissive cathode 22 and an anode 24, also indicating the parallel x-ray distribution as mentioned above.

There is therefore a need for an improved x-ray source and corresponding system that at least alleviates the prior art reliability problems, with further focus on low cost applications.

SUMMARY OF THE INVENTION

According to an aspect of the invention, the above is at least partly alleviated by an x-ray source configured to provide an omnidirectional transmission of x-ray radiation, the x-ray source comprising an anode, a field emission cathode, an evacuated chamber transparent to x-ray radiation, the anode and the field emission cathode being arranged inside of the evacuated envelope, wherein the evacuated envelope is an extended tube shaped evacuated chamber, the field emission cathode is arranged adjacently to an inside surface of the extended tube shaped evacuated chamber, and the anode is centrally arranged inside of the extended tube shaped evacuated chamber.

Another aspect of the invention is to minimize or at least significantly reduce the x-rays being absorbed into the anode as discussed above, as well as making use of as much as possible of the generated radiation The general use of the x-ray source according to the invention is for, during operation, achieving useful x-ray radiation within a large area surrounding the x-ray source. In conjunction to prior art, the field emission cathode is arranged adjacently to the inside surface of the evacuated chamber, rather than common solutions where the cathode normally is arranged centrally. In a typical prior art arrangement with the anode arranged on the inner surface of the enclosure, the electrons will impact the anode, x-rays will be generated, but since the anode in such a prior art arrangement preferably be made of a heavy element such as tungsten, it is unavoidable that the x-rays generated immediately (to a large extent) will be absorbed in the anode, and the overall efficiency of such a prior art arrangement will thus be decreased.

Another advantage with such an arrangement is an increased surface area for the field emission cathode, thereby allowing for a larger anode to be exposed to electrons transmitted from the field emission cathode. As a consequence of the inventive arrangement of the anode "surrounded" by the field emission cathode, it may according to the invention be possible to generate omnidirectional radiation of x-rays more efficiently as compared with a solution where the cathode is arranged in the center.

During operation of the x-ray source, an electrical potential is applied between the cathode and the centrally arranged anode, and electrons are consequently emitted from the cathode and accelerated to a high velocity in a direction towards the anode. Once the electrodes collide with the anode, x-rays are created. The x-rays are in then emitted from the anode in "all directions" as the field emission cathode arranged at the inner surface of the tube shaped chamber essentially "surrounds" the anode.

The anode is of a metal material, for example comprising tungsten or a more crack-resistant alloy of rhenium (5%) and tungsten (95%), or molybdenum. Other metal materials are also possible, including for example copper and cobalt. As understood from the above, the present x-ray source where the cathode is arranged to substantially surround the centrally arranged anode may thus allow for an x-ray source to be formed where the total surface of the cathode may be larger than in comparison to prior art solutions, thus possibly allowing for an increased emission of electrons towards the anode.

In a preferred embodiment of the invention, the field emission cathode is substantially transparent to x-ray radiation, for example provided as a transmission cathode. Accordingly, there will not be necessary to include a specifically arranged "window" as is common in relation to prior art x-ray source solutions. In addition, the fact that the field emission cathode is substantially transparent allows for a full omnidirectional emission of x-ray radiation. It should however be noted that it could be possible and within the concept of the present invention to allow some portions of the cathode surface to be "shield off" the x-ray radiation, for example to limit emission of x-ray radiations in one or a plurality of selected directions.

In some embodiments of the invention, the anode has an extended form matching to and extending along at least a portion of the inside of the extended tube shaped evacuated chamber, preferably manufactured from a glass material. In case of e.g. a copper target configured as the anode, the copper target may be constructed as a solid cylinder matching the tube shaped evacuated chamber.

Preferably, the x-ray source is configured to be connected to a controllable high voltage source for providing the above mentioned potential difference between the cathode and the anode. The high voltage source is electrically connected to the anode and the cathode and preferably configured to deliver a high voltage between (at least) 4-20 kV. Advantageously, the x-ray source may be adapted for generating a spectrum for the x-radiation up to approximately 20 keV when providing a current of as low as 1 mA. Accordingly, a suitable x-ray source may be provided with only small energy consumption, thus making the operation of the x-ray source cost efficient.

Preferably, the evacuated chamber has a pressure of approximately $10^{-4}$ Pa or lower to enable the use of a cold cathode using field emission and to avoid issues with degradation, lifetime arcing and similar phenomena associated with a poor vacuum in such devices.

In an embodiment of the invention the field emission cathode comprises a plurality of nanostructures. The synergistic effects provided thereby allow for improved electron emission towards the anode, and thus an improved and energy efficient generation of x-rays as compared to prior art. In the present context, the term nanostructure refers to a structure where at least one dimension is on the order of up to a few hundreds of nanometers. Such nanostructures may for example include nanotubes, nanorods, nanowires, nanopencils, nanospikes, nanoflowers, nanobelts, nanoneedles, nanodisks, nanowalls, nanofibres and nanospheres. Furthermore, the nanostructures may also be formed by bundles of any of the aforementioned structures. The preferred direction of the nanostructures is in a direction essentially perpendicular to the inner surface of the elongated tubs shaped chamber. According to one embodiment of the invention the nanostructures may comprise ZnO nanorods.

According to an alternative embodiment of the invention the nanostructure may include carbon nanotubes. Carbon nanotubes may be suitable as field emitter nanostructures in part due to their elongated shape which may concentrate and produce a higher electric field at their tips and also due to their electrical properties.

According to a further preferred embodiment, the above discussed x-ray source is preferably provided as a component in an x-ray system, wherein the x-ray system preferably also comprises the controllable high voltage power supply electrically connected to the x-ray source for powering the x-ray source.

The x-ray system may additionally comprise a control unit for controlling the operation of the power supply, possibly also in communicative connection with at least one sensor adapted for monitoring an environmental variable and as a response controlling the voltage level. The environmental variable may for example be a level of microorganisms present in a liquid or gas, such as in water or in the air.

Accordingly, in a preferred embodiment the x-ray system is configured for treatment of a liquid, such as water and consequently the x-ray system further comprises a waterproof arrangement for positioning the x-ray source in an aquatic environment. Such an embodiment may further comprise an inlet for receiving a flow of a contaminated liquid, and an outlet for outputting a flow of the treated liquid, wherein x-ray radiation is omnidirectionally irradiated towards the flow of the contaminated liquid. As such, the liquid, such as water, may be disinfected using the controlled exposure to x-ray radiation. In water, the creation of hydroxyl radicals by the ionizing radiation may be more important in the decontamination process than the direct influence of the radiation on the microorganisms directly.

The extended tube shaped chamber preferably has a circular symmetry, thereby in all essence corresponding to a typical symmetry of a water pipe, thus making the structural form of the x-ray source according to the invention specifically useful for use in regards to transportation of liquids.

Alternatively, the x-ray system may further comprise a process air path for receiving a flow of a contaminated air, and means for arranging the x-ray source within the process air path, wherein x-ray radiation is omnidirectionally irradiated towards an airflow in the process air path. In a similar manner as in regards to treatment of water, the stream of air may e.g. be disinfected using the controlled exposure to x-ray radiation.

In a possible embodiment of the invention, the x-ray source is arranged as a component of an electrostatic precipitator, further comprising at least one collection plate. The x-ray source may in such an embodiment be used for electrically charging particles comprised in the air flow passing through the process air path. The collection plate is provided with a corresponding charge for collection of the charged particles, thus effectively acting as an air purifier. Such a system may additionally comprise a filter media for collection of particles, wherein the filter media is arranged downstream of the x-ray source in a direction of the air flow. The power supply comprised with the inventive system may also be electrically connected to the at least one collection plate, thus removing the necessity of using further power sources and as a result giving the possibility manufacturing and operation of such a system at an in comparison low cost.

The above discussed x-ray system may be portable and thus may comprise a battery operated, high voltage power supply, advantageously allowing the x-system to be mobile for field applications.

Further features of, and advantages with, the present invention will become apparent when studying the appended claims and the following description. The skilled addressee realize that different features of the present invention may be combined to create embodiments other than those described in the following, without departing from the scope of the present invention.

BRIEF DESCRIPTION OF THE DRAWINGS

The various aspects of the invention, including its particular features and advantages, will be readily understood from the following detailed description and the accompanying drawings, in which.

DETAILED DESCRIPTION

The present invention will now be described more fully hereinafter with reference to the accompanying drawings, in which currently preferred embodiments of the invention are shown. This invention may, however, be embodied in many different forms and should not be construed as limited to the embodiments set forth herein; rather, these embodiments are provided for thoroughness and completeness, and fully convey the scope of the invention to the skilled addressee. Like reference characters refer to like elements throughout.

Figures 3A, 3B:
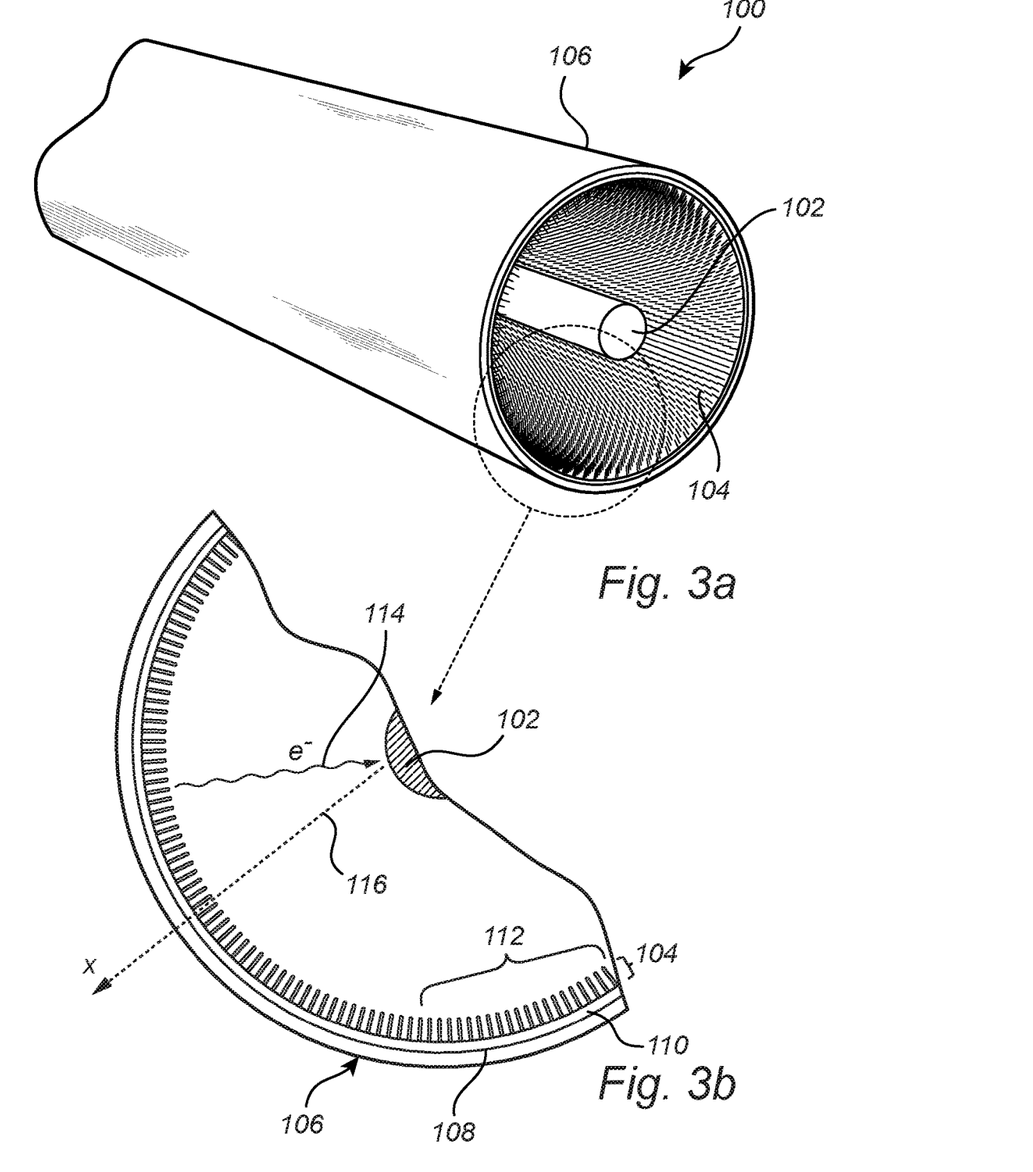
FIGS. 3a and 3b illustrate an x-ray source according to a currently preferred embodiment of the invention.

Referring now to the drawings and to FIGS. 3a and 3b in particular, there is depicted an x-ray source 100. The x-ray source 100 comprises an anode 102, a field emission cathode 104, and an evacuated chamber 106. The evacuated chamber 106 is preferably manufactured from a glass material, having a thickness and chemical construction allowing the evacuated chamber to be transparent to x-ray radiation.

The anode 102 as well as the field emission cathode 104 are arranged inside of the evacuated envelope 106 and the field emission cathode 104 is provided on an inside surface 108 of the evacuated chamber 106. The field emission cathode 104 in turn comprises an electrically conducting and x-ray transparent substrate 110 arranged on the inside surface 108. The substrate 110 may for example comprise indium tin oxide (ITO), having a thickness selected to allow for x-ray radiation to pass through.

The field emission cathode 104 further comprises a plurality of field emitters, such as a large plurality of nanostructures 112, for example selected as to comprise ZnO nanorods or carbon nanorods. The length of the nanostructures 112 is preferably selected to be at least 1 µm.

The anode 102 is preferably of a metal material, such as copper, tungsten etc. In the illustrated embodiment, the evacuated chamber 106 is constructed as an elongated chamber having a tube shape. Correspondingly, the anode 102 is selected as an elongated copper rod extending throughout the evacuated chamber 106. The x-ray source 100 is closed in each of the ends of its extension, for example using pump stems (not shown) arranged at each end. The pump stem allows for a vacuum to be created inside of the chamber, preferably having a pressure of approximately $10^{-4}$ Pa or lower. The pump stems are preferably also of glass and welded to the tube shaped chamber 106.

The pump stems may further be configured for allowing an electrical connection between a power supply (not shown) and the anode 102/cathode 104. The power supply is as mentioned above preferably configured to at least allow control of a voltage level provided to the x-ray source. The power supply may additionally be configured to receive data from at least one sensor, the data being indicative of an environmental variable surrounding the x-ray source 100, for consequent regulation of the voltage level.

During operation of the x-ray source 100, the power supply will provide the controlled high voltage to the anode 102 and the cathode 104. An electrical field is created between the outer ends of the plurality of nanostructures 112 and the anode 102, whereby electrons 114 will be transmitted and impinge onto the surface of the centrally arranged anode 102. Once the electrons 114 are received by the anode 102, x-rays 116 will be irradiated. As the cathode 104 is arranged to essentially surround the anode 102, the electrons 114 will be received "on all sides" of the anode 102, and thus x-rays 116 will be transmitted in all directions (e.g. 360 degrees), omnidirectionally, from the anode 102.

The x-rays 116 are as a consequence of the implementation of the x-ray source 100 transmitted towards the cathode 104, and pass through the cathode 102 and outside of the chamber 106 to the external surrounding of the x-ray source 100. The field emission cathode 104 may thus be implemented as a transmission cathode.

Figures 4A, 4B:
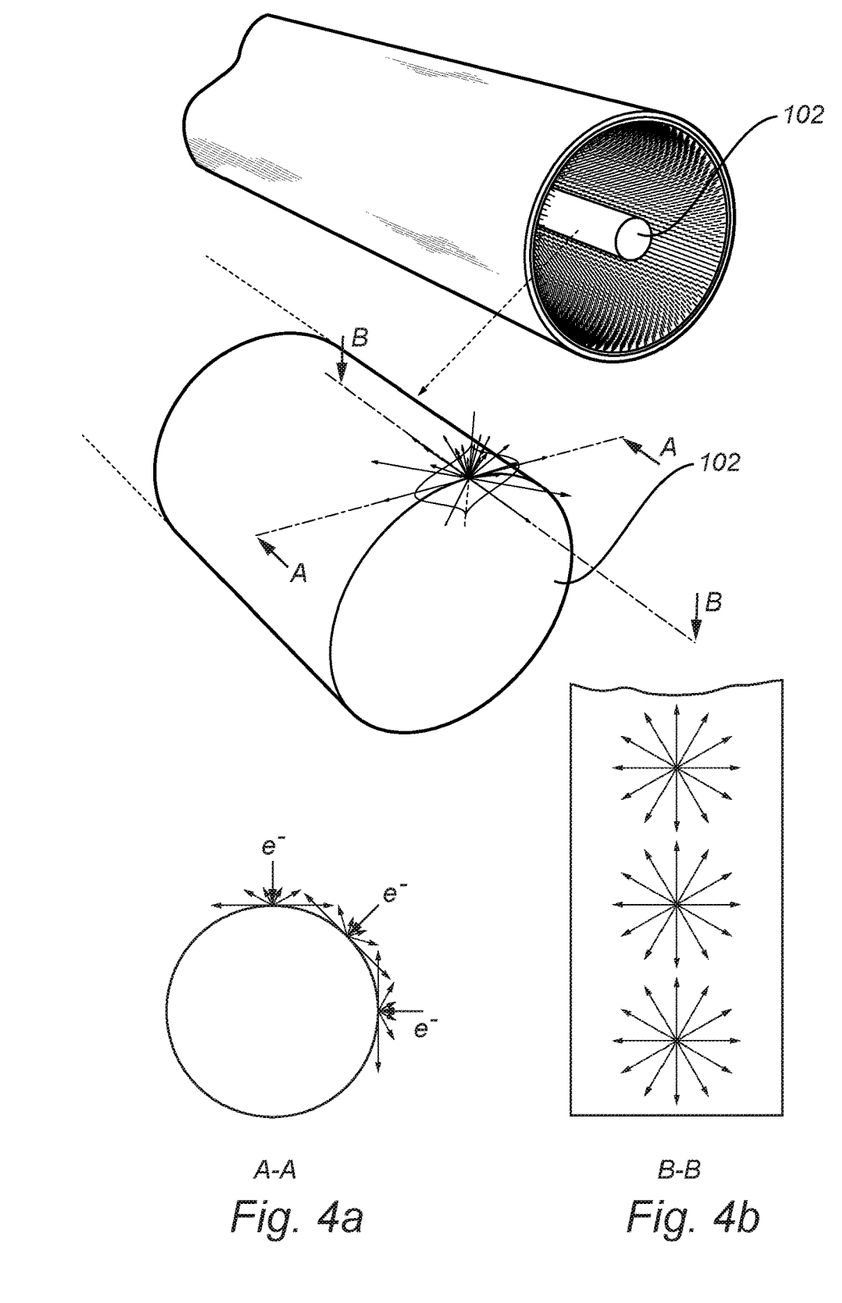
FIGS. 4a-4b illustrate the x-ray distribution pattern generated in a x-ray source according to the invention.

Turning to FIGS. 4a and 4b for a further explanation in regards to the results achieved according to the invention. As discussed above, the bremsstrahlung radiation intensity maximum is perpendicular to the electron path), while the characteristic radiation has a uniform intensity distribution over a full solid angle (spherical). By making use of the inventive concept where the evacuated chamber 106 is specifically selected to have a tube shaped form, and the anode 102 is centrally arranged inside of the extended tube shaped evacuated chamber 106, it is possible to achieve a uniform distribution pattern "surrounding" the anode 102 in a manner as is shown in FIGS. 4a and 4b. In comparison to the flat x-ray source shown in FIG. 2, the inventive x-ray source 100 according to the invention only "loose" a limited amount of the x-ray radiation in a lateral direction. Thus is due to the fact that the anode 102 in one point in relation to the cathode 104 is essentially placed at an angle to the cathode 104 as is discussed in relation to FIGS. 1a and 1b. Thus, only the lateral x-ray radiation in the direction of the extension of the anode 102 will be lost from being radiated outside of the x-ray source 100.

Figure 5:
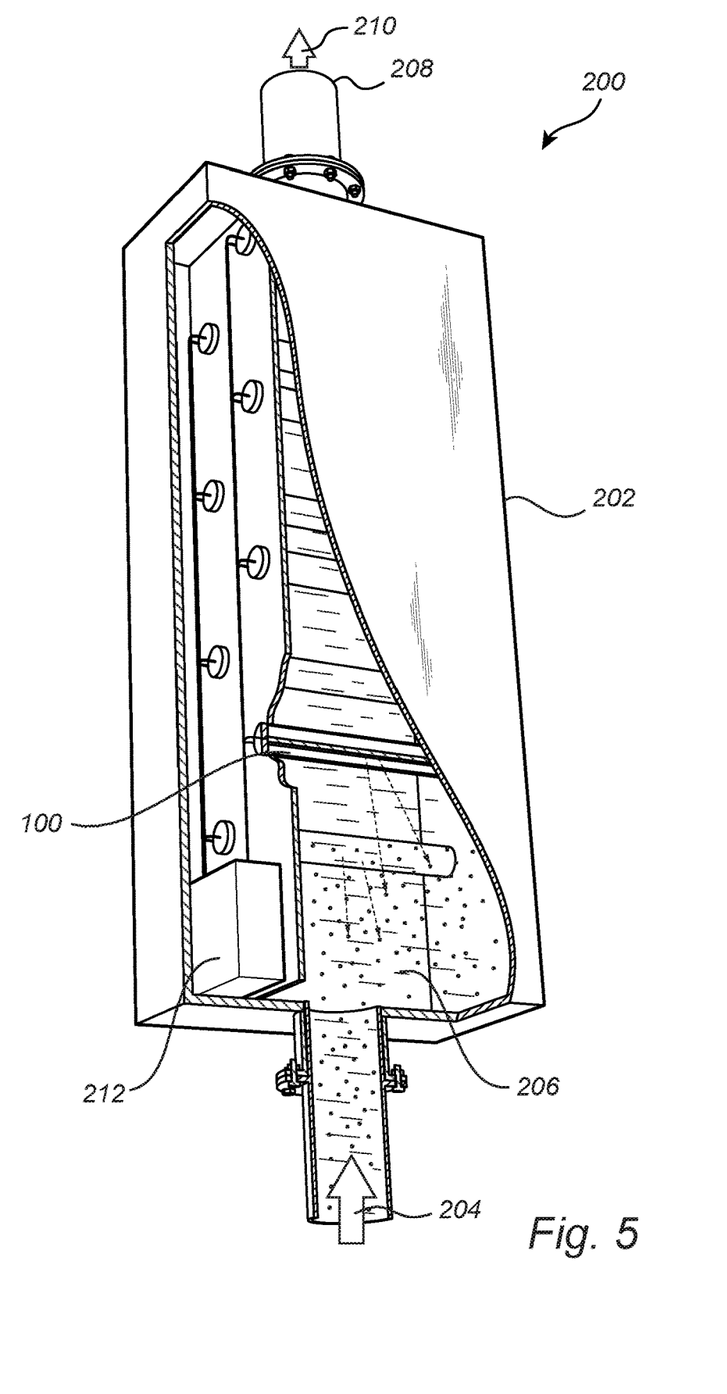
FIG. 5 shows an example of an x-ray system configured for water treatment.

Turning now to FIG. 5, which illustrates a possible implementation of an x-ray system 200 comprising a plurality of x-ray sources 100 according to the invention. The x-ray system 200 is in the illustrated embodiment of FIG. 5 exemplified as an arrangement for water purification. As such, the x-ray system 200 comprises a body 202 shaped to have a rectangular cross-section, having an inlet 204 arranged at one end and configured to be connected to e.g. a pump (not shown) for transportation of a flow of a contaminated water 206 into the system 200. The system 200 also comprises an outlet 208 arranged at another end of the body 202 for outputting at least partly purified water 210.

The plurality of x-ray sources 100 are arranged in a zig-zag pattern within the rectangular body 202 such that the contaminated water 206 sequentially will pass by the x-ray sources 100. Turbulence and mixing generating means (not shown) may be provided inside of the body 202 for improving the "contact" between x-rays emitted by the x-ray sources 100 and the contaminated water 206, where the turbulence and mixing generating means are selected from one or more of the means from the group consisting of perforations, holes, punchings, structured pressings, corrugations, and grooves. Further types of turbulence and mixing generating means are possible and within the scope of the invention. The same accounts for the positioning of the x-ray sources 100 within the system 200, e.g. by arranging the x-ray sources 100 in single or double columns, etc. In the illustrated embodiment, eight x-ray sources 100 are shown. It is understood that any number of x-ray sources 100 may be provided (also a single one) depending on the implementation of the system 200.

Once x-ray radiation comes in contact with contaminated water 206, possibly containing bacteria and microorganisms, a process will initiate where the cells of the bacteria/microorganisms will break down and thereby kill the bacteria/microorganisms, such that at least partly purified water 210 may be outputted throughout the outlet 208.

The system 200 shown in FIG. 5 may for example be used for wastewater treatment or for use in a ballast water implementation. Other implementations are of course possible and within the scope of the invention. Similarly, the description provided in relation to FIG. 5 has been made with reference to water. Other liquids are in a similar manner possible and within the scope of the invention. Also, a control unit 212 is provided for controlling the power supply and possibly receiving the measurement of an environmental variable from a sensor (not shown), such as a level of bacteria/microorganisms available at (essentially) the output of the body 202, may be used for controlling the voltage level and thus the potential difference provided between the anode 102 and the cathode 104 of the x-ray sources 100. In addition, the control unit 212 may be configured to control a valve (not shown), e.g. arranged downstream of the outlet 208. By adjusting the level of opening of such a valve, the time the contaminated water 206 is exposed to the x-ray radiation may be adjusted.

Figure 6:
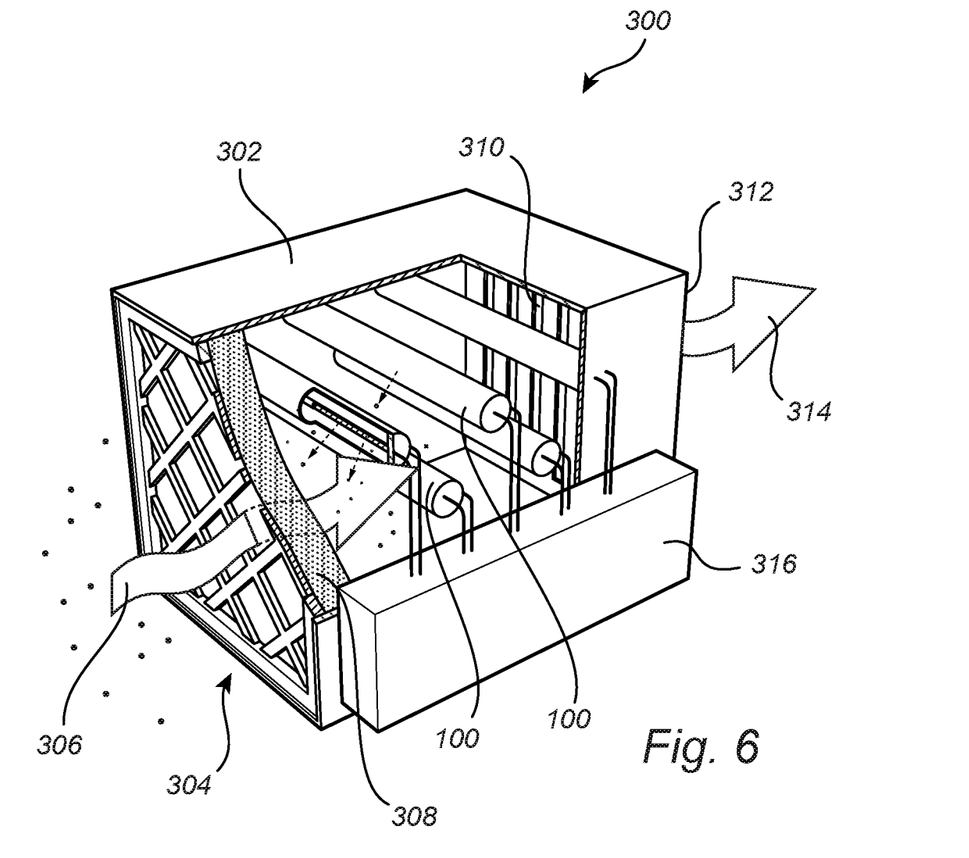
FIG. 6 provides an alternative x-rays system configured for air treatment.

In an alternative embodiment of the invention with reference to FIG. 6, a dust collection system 300 for air purification is provided. The system 300 comprises a body 302 having an inlet 304 configured to receive a contaminated air flow 306 containing a plurality of particles. A filter media 308 is comprised with the system 300 for filtering out "coarse" particles. The system 300 is also provided with a plurality of x-ray sources 100 as discussed above and provided for omnidirectional irradiation of x-rays towards the air flow.

In the illustrated exemplified implementation provided in FIG. 6, the radiation of x-rays will charge the particles remaining after the filter media 308, and a plurality of collection plates 310 are arranged in the vicinity of an outlet 312 of the body 302. The particles in the air flow being charged by the x-ray radiation from the x-ray sources 100 and subsequently collected by the collection plates 310 and then outputted through the 312 as a purified air stream 314. Accordingly, the collection plates are correspondingly provided with an electrical potential (in comparison to the charged particles) for allowing the discussed particle collection.

The above discussion in regards to the dust collection system 300 has been provided in relation to air; however any type of gas would be possible and is within the scope of the invention. In addition, a fan (not shown) is typically provided for forcing air/gas through the dust collection system 300. The purified air stream 314 may subsequently be provided as an input to an air conditioning arrangement for a building, vehicle or the like.

In a similar manner as discussed above, a control unit 316 is provided for controlling the power supply and possibly receiving the measurement of an environmental variable from a sensor (not shown), such as a level of bacteria/microorganisms available at (essentially) the output of the body 302, may be used for controlling the voltage level and thus the potential difference provided between the anode 102 and the cathode 104 of the x-ray sources 100.

In summary, the present invention relates to an x-ray source configured to provide an omnidirectional transmission of x-ray radiation, the x-ray source comprising an anode, a field emission cathode, an evacuated chamber transparent to x-ray radiation, the anode and the field emission cathode being arranged inside of the evacuated envelope, wherein the evacuated envelope is an extended tube shaped evacuated chamber, the field emission cathode is arranged adjacently to an inside surface of the extended tube shaped evacuated chamber, and the anode is centrally arranged inside of the extended tube shaped evacuated chamber.

The general use of the x-ray source according to the invention is for, during operation, achieving useful x-ray radiation within a large area surrounding the x-ray source. In conjunction to prior art, the field emission cathode is arranged adjacently to the inside surface of the evacuated chamber, rather than common solutions where the cathode normally is arranged centrally. The advantages with such an arrangement are increase surface area for the field emission cathode, thereby allowing for a larger anode to be exposed to electrons transmitted from the field emission cathode. As a consequence of the inventive arrangement of the anode "surrounded" by the field emission cathode, it may according to the invention be possible to generate omnidirectional radiation of x-rays.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps. Additionally, even though the invention has been described with reference to specific exemplifying embodiments thereof, many different alterations, modifications and the like will become apparent for those skilled in the art.

Variations to the disclosed embodiments can be understood and effected by the skilled addressee in practicing the claimed invention, from a study of the drawings, the disclosure, and the appended claims. Furthermore, in the claims, the word "comprising" does not exclude other elements or steps, and the indefinite article "a" or "an" does not exclude a plurality.

The invention claimed is:

1. An x-ray source configured to provide an omnidirectional transmission of x-ray radiation, the x-ray source comprising:
    an anode;
    a field emission cathode;
    an evacuated chamber transparent to x-ray radiation, the anode and the field emission cathode being arranged inside of the evacuated envelope,
    wherein the evacuated envelope is an extended tube shaped evacuated chamber having an essentially circular symmetry, the field emission cathode is arranged adjacently to an inside surface of the extended tube shaped evacuated chamber, and the anode is centrally arranged inside of the extended tube shaped evacuated chamber,
    the field emission cathode surrounds the anode,
    the field emission cathode comprises a plurality of ZnO nanostructures selected to be at least 1 micrometer,
    the field emission cathode is substantially transparent to X-ray radiation and formed as a transmission cathode, and
    the x-ray source is connected to a controllable high voltage source, electrons during operation of the x-ray source are accelerated from the field emission cathode in a direction towards the anode, and x-ray radiation is omnidirectionally irradiated from the anode towards and through the field emission cathode and out from the x-ray source.

2. The x-ray source according to claim 1, wherein the anode has an extended form matching to and extending along at least a portion of the inside of the extended tube shaped evacuated chamber.

3. The x-ray source according to claim 1, wherein the field emission cathode comprises a plurality of nanostructures.

4. An x-ray system, comprising:
    the x-ray source according to claim 1, and
    a controllable high voltage power supply connected to the x-ray source for powering the x-ray source.

5. The x-ray system according to claim 4, further comprising a control unit for controlling the operation of the power supply.

6. The x-ray system according to claim 4, further comprising a waterproof arrangement for positioning the x-ray source in an aquatic environment.

7. The x-ray system according to claim 6, further comprising:
    an inlet for receiving a flow of a contaminated liquid; and
    an outlet for outputting a flow of the treated liquid,
    wherein x-ray radiation is omnidirectionally irradiated towards the flow of the contaminated liquid.

8. The x-ray system according to claim 4, further comprising
    a process air path for receiving a flow of a contaminated air; and
    means for arranging the x-ray source within the process air path,
    wherein x-ray radiation is omnidirectionally irradiated towards an airflow in the process air path.

9. The x-ray system according to claim 8, wherein the x-ray source is a component of an electrostatic precipitator, the electrostatic precipitator further comprising at least one collection plate.

10. The x-ray system according to claim 9, wherein the x-ray system is an air purifier.

11. The x-ray system according to claim 8, further comprising a filter media for collection of particles, wherein the filter media is arranged upstream of the x-ray source in a direction of the air flow.

* * * * *